United States Patent
Jung, Jr. et al.

(10) Patent No.: US 11,090,006 B2
(45) Date of Patent: Aug. 17, 2021

(54) MODULAR SENSING GUIDEWIRE

(71) Applicants: Eugene J Jung, Jr., San Diego, CA (US); Reza S Mohammadpour, Mentor, OH (US); Subbakrishna Shankar, Shaker Hts, OH (US); Mohamed Lababidi, Cleveland, OH (US)

(72) Inventors: Eugene J Jung, Jr., San Diego, CA (US); Reza S Mohammadpour, Mentor, OH (US); Subbakrishna Shankar, Shaker Hts, OH (US); Mohamed Lababidi, Cleveland, OH (US)

(73) Assignee: CORMETRICS LLC, Shaker Hts., OH (US)

( * ) Notice: Subject to any disclaimer, the term of this patent is extended or adjusted under 35 U.S.C. 154(b) by 0 days.

(21) Appl. No.: 15/424,261

(22) Filed: Feb. 3, 2017

(65) Prior Publication Data

US 2017/0215801 A1 Aug. 3, 2017

Related U.S. Application Data

(60) Provisional application No. 62/290,779, filed on Feb. 3, 2016, provisional application No. 62/379,814, filed on Aug. 26, 2016.

(51) Int. Cl.
*A61B 5/00* (2006.01)
*A61B 5/02* (2006.01)
*A61B 5/0215* (2006.01)

(52) U.S. Cl.
CPC ........ *A61B 5/6851* (2013.01); *A61B 5/02007* (2013.01); *A61B 5/0215* (2013.01);
(Continued)

(58) Field of Classification Search
CPC . A61B 5/6851; A61B 5/0215; A61B 2562/22; A61B 2560/0043
See application file for complete search history.

(56) References Cited

U.S. PATENT DOCUMENTS 4,238,217 A 12/1980 Stepanek et al.
4,257,675 A 3/1981 Nakagome et al.
(Continued)

FOREIGN PATENT DOCUMENTS

DE 2919615 A1 12/1980

*Primary Examiner* — Sean P Dougherty

(57) ABSTRACT

A sensing guidewire device used to measure physiological parameters within a living body. In one embodiment, the device is used to measure the fractional flow reserve (FFR) across a stenotic lesion in a patient's vasculature. The device includes a sensor that is adapted to be affixed near the distal end of a guidewire. The guidewire contains a corewire, processed to enclose electrical conductors in a sealed, off-centered interstice or channel, with an outer diameter approximate to the outer diameter of the device, running substantially the full length of the device, and has a homogenous outer surface. The enclosed eccentric channel provides space for electrical conductors to move freely. The corewire can have a tapered segment to create desirable flexibility. A solid connector comprised of alternating conductive and insulating elements for connecting the conductors to an external device is disclosed. The guidewire can be advanced through a patient's blood vessels, returning pressure measurements across vessel blockages that allow for accurate assessment of blockage severity and lead to better clinical outcomes.

15 Claims, 13 Drawing Sheets

(52) U.S. Cl.
CPC ... *A61B 2560/0443* (2013.01); *A61B 2562/12* (2013.01); *A61B 2562/22* (2013.01)

(56) References Cited

U.S. PATENT DOCUMENTS

| | | | |
|---|---|---|---|
| 4,389,088 A | 6/1983 | Trezequet | |
| 4,481,953 A | 11/1984 | Gold et al. | |
| 4,958,642 A | 9/1990 | Christian et al. | |
| 4,961,433 A | 10/1990 | Christian | |
| 5,105,818 A | 4/1992 | Christian et al. | |
| 5,178,159 A | 1/1993 | Christian | |
| 5,226,423 A | 7/1993 | Tenerz et al. | |
| 5,333,625 A | 8/1994 | Klein | |
| 5,406,960 A | 4/1995 | Corso, Jr. | |
| 5,517,989 A | 5/1996 | Frisbie et al. | |
| 5,715,827 A | 2/1998 | Corl et al. | |
| 5,779,644 A | 7/1998 | Eberle et al. | |
| 5,867,974 A | 2/1999 | Schmid | |
| 5,938,615 A | 8/1999 | Eberle et al. | |
| 5,938,624 A | 8/1999 | Akerfeldt et al. | |
| 6,112,598 A | 9/2000 | Tenerz et al. | |
| 6,196,980 B1 | 3/2001 | Akerfeldt et al. | |
| 6,248,083 B1 | 6/2001 | Smith et al. | |
| 6,377,052 B1 | 4/2002 | McGinnis et al. | |
| 6,551,250 B2 | 4/2003 | Khalil | |
| 6,582,536 B2* | 6/2003 | Shimada | A61M 25/0012 148/519 |
| 6,615,667 B2 | 9/2003 | Smith | |
| 6,754,608 B2 | 6/2004 | Svanerudh et al. | |
| 6,976,965 B2 | 12/2005 | Corl et al. | |
| 8,226,578 B2 | 7/2012 | Von Malmborg | |
| 8,277,386 B2 | 10/2012 | Ahmed et al. | |
| 8,298,156 B2 | 10/2012 | Manstrom et al. | |
| 8,419,647 B2 | 4/2013 | Corl et al. | |
| 8,548,778 B1 | 10/2013 | Hart et al. | |
| 8,551,022 B2 | 10/2013 | Von Malmborg | |
| 8,556,820 B2 | 10/2013 | Alpert et al. | |
| 8,617,088 B2 | 12/2013 | Samuelsson et al. | |
| 8,641,633 B2 | 2/2014 | Smith | |
| 8,852,125 B2 | 10/2014 | Von Malmborg | |
| 9,427,551 B2* | 8/2016 | Leeflang | A61M 25/0012 |
| 9,974,617 B2* | 5/2018 | Flexman | G02B 23/2476 |
| 10,258,240 B1* | 4/2019 | Eberle | A61B 5/0084 |
| 2001/0027261 A1* | 10/2001 | Ciezki | A61N 5/1002 600/3 |
| 2003/0088193 A1 | 5/2003 | Von Malmborg | |
| 2003/0220588 A1* | 11/2003 | Tenerz | A61B 5/6851 600/585 |
| 2004/0064024 A1* | 4/2004 | Sommer | A61N 1/056 600/374 |
| 2005/0272975 A1* | 12/2005 | McWeeney | A61B 1/00071 600/113 |
| 2006/0074318 A1 | 4/2006 | Ahmed et al. | |
| 2006/0106298 A1* | 5/2006 | Ahmed | A61B 5/0422 600/381 |
| 2006/0241505 A1 | 10/2006 | Ahmed et al. | |
| 2007/0208252 A1* | 9/2007 | Makower | A61B 5/6851 600/424 |
| 2008/0077050 A1* | 3/2008 | Von Malmborg | A61B 5/6851 600/585 |
| 2009/0192412 A1* | 7/2009 | Sela | A61B 5/06 600/585 |
| 2010/0228112 A1 | 9/2010 | Von Malmborg | |
| 2010/0318000 A1* | 12/2010 | Von Malmborg | A61B 5/0215 600/585 |
| 2012/0265079 A1 | 10/2012 | Hilmersson | |
| 2012/0277671 A1* | 11/2012 | Fuentes | A61M 25/005 604/95.04 |
| 2013/0096455 A1* | 4/2013 | Kassab | H01B 7/048 600/547 |
| 2013/0237864 A1 | 9/2013 | Mazar et al. | |
| 2013/0296692 A1* | 11/2013 | Vanney | A61M 25/09 600/424 |
| 2013/0317372 A1 | 11/2013 | Eberle | A61B 5/02154 600/478 |
| 2014/0005543 A1* | 1/2014 | Burkett | A61B 5/6851 600/437 |
| 2014/0180080 A1 | 6/2014 | Mittal et al. | |
| 2014/0180141 A1* | 6/2014 | Millett | A61B 5/0215 600/486 |
| 2014/0180143 A1* | 6/2014 | Millett | A61B 5/0215 600/488 |
| 2014/0187972 A1* | 7/2014 | Burkett | A61B 5/02055 600/481 |
| 2014/0275892 A1 | 9/2014 | Manstrom et al. | |
| 2014/0276028 A1 | 9/2014 | Stigall et al. | |
| 2014/0276198 A1* | 9/2014 | Dunung | A61B 5/036 600/561 |
| 2014/0276223 A1 | 9/2014 | Gustafsson | |
| 2015/0025398 A1 | 1/2015 | Davies et al. | |
| 2015/0051696 A1* | 2/2015 | Hou | A61F 2/2427 623/2.11 |
| 2015/0073252 A1 | 3/2015 | Mazar | |
| 2015/0074995 A1* | 3/2015 | Patil | A61B 5/6851 29/855 |
| 2015/0141854 A1* | 5/2015 | Eberle | A61B 5/02154 600/488 |
| 2015/0217090 A1* | 8/2015 | Burkett | A61B 18/1492 600/301 |
| 2015/0273181 A1 | 10/2015 | Leeflang et al. | |
| 2015/0306806 A1* | 10/2015 | Dando | A61M 25/0009 264/515 |
| 2016/0128583 A1* | 5/2016 | Caron | A61B 5/042 600/486 |
| 2017/0027458 A1* | 2/2017 | Glover | A61B 5/743 |
| 2017/0181646 A1* | 6/2017 | Hayes | A61B 5/6851 |
| 2018/0228385 A1* | 8/2018 | Eberle | A61B 5/6851 |

* cited by examiner

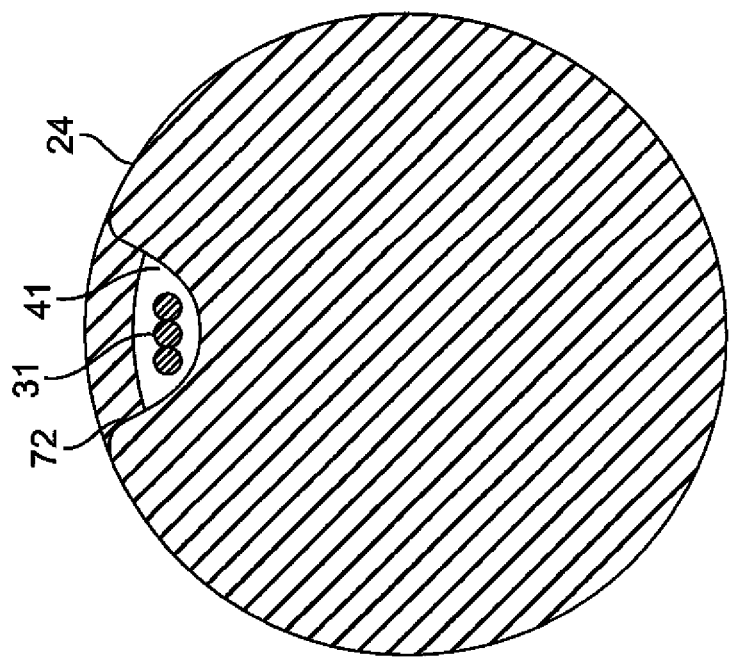
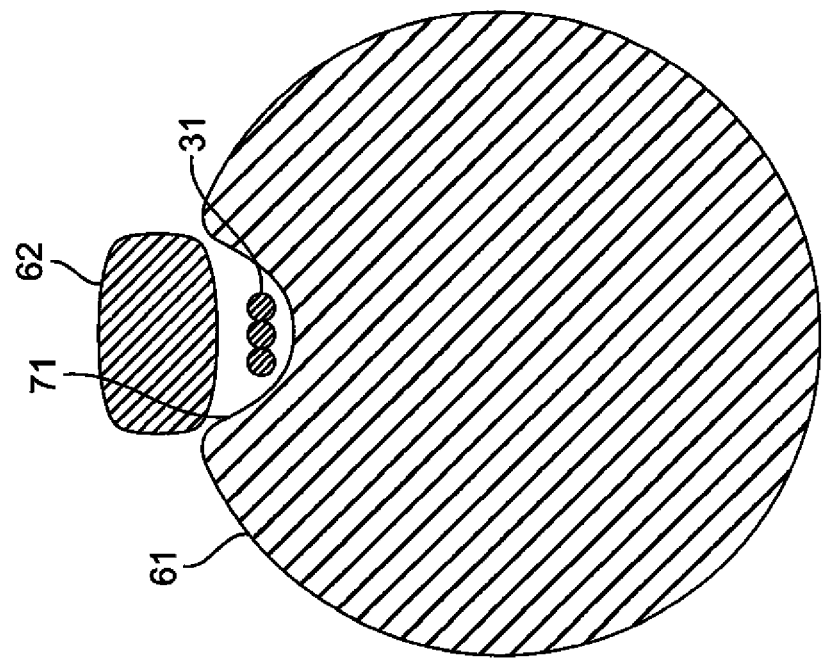
FIG. 7A
FIG. 7B

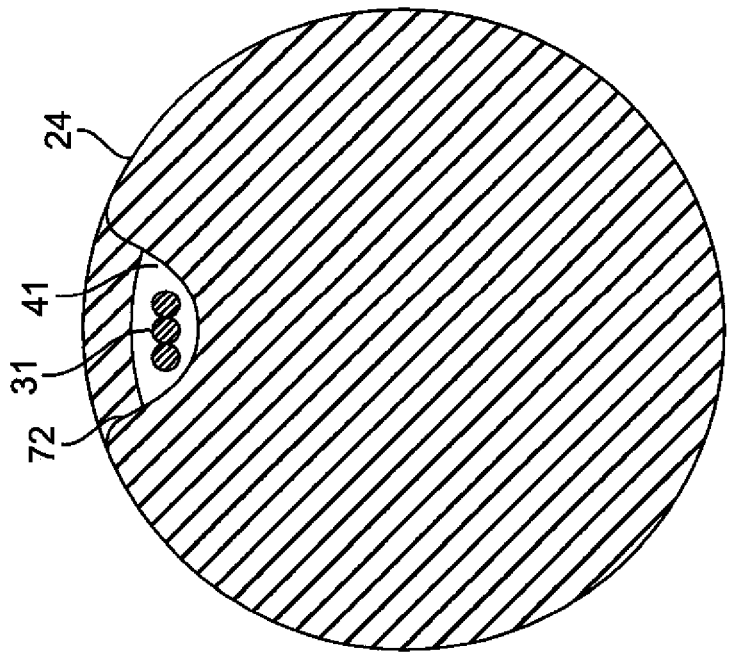
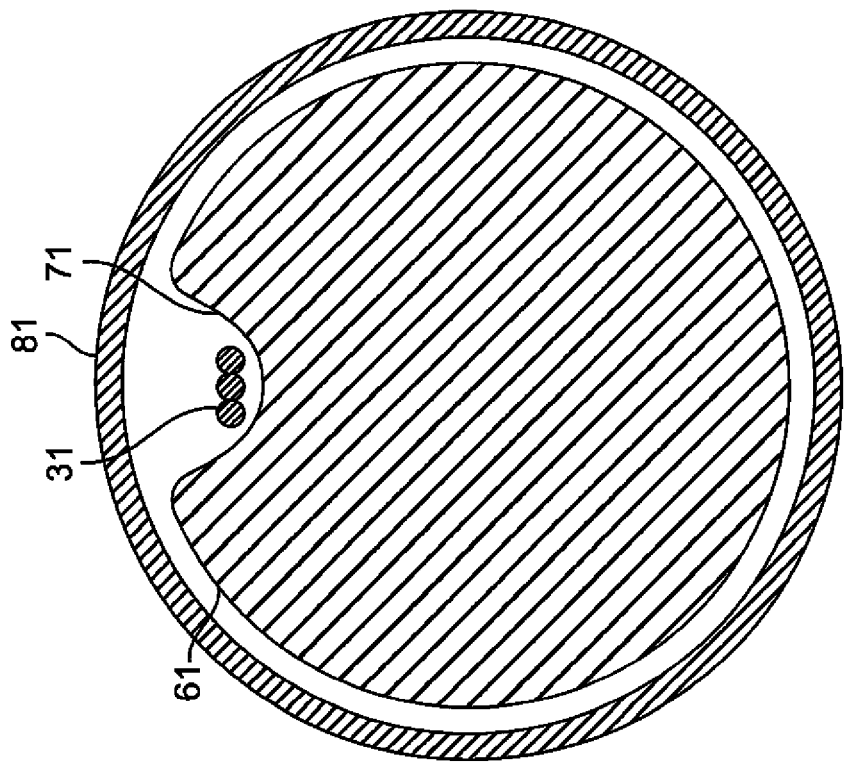

MODULAR SENSING GUIDEWIRE

CROSS-REFERENCE TO RELATED APPLICATIONS

This application claims priority from U.S. Provisional patent application No. 62/290,779 entitled "Guidewire with sensor", filed Feb. 3, 2016, and from U.S. Provisional patent application No. 62/379,814 entitled "Modular Sensing Guidewire", filed Aug. 26, 2016, both of which are incorporated herein by reference in their entirety.

FIELD OF THE INVENTION

This invention relates generally to the field of measuring physiological parameters within a living body.

BACKGROUND OF THE INVENTION

While there are different ways to measure physiological parameters, the most accurate measurements often require having the sensor in close physical proximity to the anatomy of interest. Characterizing stenotic lesions within a blood vessel can be done by passing a sensor through the stenotic lesion to measure directly pressure drop or other physiological parameters. In minimally invasive non-surgical techniques, the way to gain access to the anatomy is by inserting a guidewire from outside a patient's body, through the patient's vasculature, to the anatomical site of interest. The guidewire's ability to successfully navigate through vasculature and across stenotic lesion sites without injury is an important performance parameter that determines user preference, whether the guidewire contains a sensor or not.

Looking at current practice for the characterization of stenotic lesions, and in particular those relating to coronary artery disease (CAD), an access guidewire is inserted into a patient's vasculature. Once a desired location has been accessed, a catheter is fed over the access guidewire which is then removed leaving the catheter in a place to facilitate advancement of a second guidewire designed for use in the coronary vasculature. This guidewire can include a sensor at its distal tip. The sensor guidewire is advanced through the catheter. Upon exiting the catheter, the sensor guidewire is advanced through the vasculature where blood pressure or other important physiological parameters are measured. Stenotic lesions are characterized by abnormal or abrupt changes in blood pressure or flow, so the device operator can identify the location of a clinically significant stenotic lesion by making a measurement before and after the blockage.

Fractional Flow Reserve (FFR) is a ratio of blood pressure measurements before and after a stenotic lesion under hyperemic conditions. Data collected using this methodology has established important thresholds for guiding therapeutic decisions. Importantly, the guidewire must be able to be advanced through the vasculature and across the lesion site to make this measurement.

Currently, treatment of stenoses in arteries is predominantly guided by x-ray imaging techniques. In interventional cardiology, one such x-ray technology is fluoroscopy. Angiography is a technique of injecting radiopaque dye into arteries using fluoroscopic equipment, which has proven to be useful in identifying stenotic lesions. However, patients with CAD often have blockages at more than one site. This creates a challenge for the operator treating the patient. An operator must correctly determine which of multiple blockages are causing the symptoms which prompted the procedure. An angiogram presents a two dimensional view of a three dimensional phenomena, blood flow through a vessel. Angiographic images can over-represent or under-represent the perceived degree of blockage. Important clinical studies have shown that patients treated using a FFR pressure wire to guide treatment instead of fluoroscopy alone have improved outcomes. These studies have shown that not treating a clinically significant stenotic lesion has a deleterious impact on patient outcomes. Less intuitively, treating stenotic lesions that are clinically insignificant also have a deleterious impact on patient outcomes. Thus, a patient afflicted with multiple stenotic lesions is best served by only treating clinically significant lesions and leaving the clinically insignificant lesions untreated. Clinical studies have consistently demonstrated that treatment guidance for blocked coronary arteries using physiological measurements have consistently outperformed image guidance alone in improving patient outcomes.

Most coronary guidewires used today do not have sensors. Non-sensing guidewires have designs optimized to cross stenotic lesions in coronary arteries. The most frequently used coronary guidewires employ a solid corewire. A solid wire enables the superior pushing capability needed to advance the device in the body, is kink resistant, and has exceptional tip control needed to navigate through bends, twists and turns in vessel vasculature. It also provides stable support for delivering catheters and stents. Stability means the coronary guidewire does not back out of the artery and lose position as therapeutic devices are advanced over the guidewire. A coronary guidewire is typically approximately 355 microns in diameter or less. Consequently, optimizing material characteristics is an important aspect in extracting maximum performance from such a miniature device. A solid corewire is typically made using a cold work forming process that enhances mechanical strength. Guidewires of this type, which are most frequently used, while optimized in design for crossing stenotic lesions lack sensing capabilities to measure abnormal pressure drops using FFR techniques, which are needed to effectively guide treatment.

Prior art patents related to guidewire capabilities are numerous, including, for example, U.S. Pat. Nos. 4,958,642 and 5,226,423, which describe guidewire assemblies with sensors and interconnect cables. While these devices enable making FFR measurements, they are less than optimal in their performance with respect to navigating through anatomy, and are expensive to manufacture. Such FFR guidewires use long, hollow tubular structures to route wires needed to connect the sensor at the tip of the wire to a processor outside the patient's body. The sensor guidewire's hollow tube is unable to be processed in the same manner as a solid corewire to enhance mechanical strength, compromising the mechanical performance of these sensing guidewires compared to non-sensing guidewires. A hollow tube's inherently lower strength makes it more susceptible to kinking, taking a curved set and generally deforming more readily than a guidewire made from a cold drawn solid corewire. Moreover, such FFR guidewires use multiple discrete components assembled together requiring expensive labor intensive processes. These designs also lack the seamless and progressive guidewire transition from stiff to flexible that traditional non-sensing guidewires offer with their unitary solid corewire construction.

In U.S. Pat. No. 5,406,960 a corewire with grooves is used in a coronary guidewire. The grooved corewire provides space to place radiopaque bands to enhance visibility under fluoroscopy.

U.S. Pat. No. 5,797,856 describes a tubular member coaxially disposed on a solid corewire to make a guidewire with improved torque transmission capabilities. However, a clearance of 0.001-0.003 inches is specified between the inner flexible member and outer tubular member, which compromises guidewire performance, given the entire guidewire outer diameter could be as small as 0.014 inches. Moreover, the outer and inner members are secured using adhesive or threading, which precludes the insertion of wiring needed to power a sensor and to transmit electrical signals from the sensor to an external instrument.

U.S. Pat. Nos. 8,231,537 and 8,277,386 describe a sensor assembly with a solid corewire with wires routed external to the solid corewire within channels in a tubular insulator. This construction yields a solid core of inadequate diameter because of the space required to contain individual conductors and a sleeve to cover them.

U.S. Patent App. No. 2010/0228112, and related U.S. Pat. Nos. 8,852,125, 8,226,578 and 8,551,022, may provide a helically grooved corewire for use in a sensor guidewire for better predictability in guidewire movement. The helical winding is intended to preclude energy from being built up during guidewire rotation. In one embodiment the electrical wires in the grooves are left uncovered in order to achieve maximal corewire outer diameter, which, however, exposes delicate electrical wiring during use, potentially reducing device reliability and increasing risk of patient injury. In another embodiment, a proximal cover is fitted over the corewire to protect the microcables. The cover reduces the outer diameter of the corewire, thereby compromising the guidewire handling performance.

U.S. Patent App. Nos. 2013/0296722 and 2013/0237864 describe a guidewire using a different electrical circuit to measure pressure which allows replacing a hollow tubular member with a solid core. Such highly miniaturized complex electrical circuit components and a sensor to fit into a guidewire, are significant and expensive technological challenges, which are difficult to overcome in today's cost constrained healthcare environment.

U.S. Patent App. No. 2015/0032027 describes a guidewire with grooves cut into a solid core using secondary processes like grinding, machining or laser etching. Insulated wires are inserted into the grooves to provide electrical conduction. How to contain the electrical wires in the grooves is not addressed, and as the electrical wires are subjected to severe bending, torque, and manipulation, such manipulation can unravel the wires set into the channels. Stress acting on the structure is greatest at the outer surface, consequently, the electrical conductors when spirally wound or adhered onto the solid core are subjected to forces that can break the wires causing device failure. Loose wires extending from a device advanced by pushing through delicate vasculature presents safety risks to the patient.

Pressure or sensor wires utilizing hollow tubes to route wires or other signal conductors necessitate the use of a connection cable to relay signals from the sensor to an external instrument. Typically, a subassembly for connection is built into the proximal most segment of the hollow tube. The interconnecting subassembly must provide for secure engagement and coupling to a cable to pass signals from the sensor to an external instrument. These couplings are prone to damage because of frail designs necessitated, in part, by the use of hollow tubes. They are also prone to failure because of susceptibility to contamination from blood, saline or other liquids commonly spilled on the device during the course of use.

Prior art sensor guidewires have significant design and performance shortcomings, and are expensive due to labor intensive assembly and manufacturing costs, and consequently represent a small fraction of the guidewires used in today's coronary interventions.

There remains a need for a sensor guidewire that can navigate tortuous vascular anatomy with the same degree of success as non-sensing guidewires. Such a device would ideally eliminate the hollow tube currently employed as a structural element, in order to improve flexibility. Moreover, an improved delivery platform utilizing existing electrical circuit and sensor components is desirable in order to reduce development expenses, commercialization timelines and device cost. A more robust and reliable connection to a cable to route signals from the pressure or sensor wire to an external instrument is needed. Additionally, there is a need for a modern technology platform, modular in construction, that reduces the manufacturing costs and provides for tailoring guidewire handling performance characteristics to provide a range of models to suit user's individual preferences.

SUMMARY OF THE INVENTION

The device of the present application utilizes a high strength corewire of a diameter and cross-sectional area approximate to a non-sensing guidewire corewire intended for the same application. This is accomplished using a novel structure including a flexible distal segment, an intermediate corewire, and an interconnecting proximal subassembly segment.

The initially solid corewire is processed so that the outer surface has a circular cross-sectional configuration, and has formed within it interstices or an internal channel or channels, which are positioned offset from the centerline of the device to accommodate electrical conductors. The internal channels are formed as a closed channel, or channels which are closed during processing, and are non-centered, non-coaxial, with respect to the central axis of the corewire. The internal channels are large enough so that the conductors can nest within them but small enough so as to preserve the mechanical integrity of the corewire. The shape of the internal channels may be of any cross-sectional configuration, but is optimized to enable high volume, cost efficient manufacturing. The device is composed of a modular assembly of building blocks that can be easily and inexpensively tailored to provide a range of performance characteristics to suit individual user preferences. The corewire functions as a structural backbone that extends substantially the full length of the sensing guidewire.

The conductors are contained within the internal channels of the corewire to protect the conductors and preserve the corewire's mechanical characteristics by maximizing the diameter of the corewire. Stress due to bending moment is zero at the neutral axis, or the center longitudinal axis of the cross-sectional area of the corewire, and increases to the largest stresses acting on the outer diameter of the corewire. Such stresses warrant extra measures to protect the relatively fragile conductors, however doing so while maximizing the corewire outer dimension requires a novel form, which has only recently been made possible by improved manufacturing techniques. This novel guidewire device with a corewire with internal closed channels also preserves the tactility of the corewire without having to assemble a separate cover over the corewire, which may require expensive secondary operations to adhere into a single form, for example, using threading or adhesives, as in the prior art.

A miniaturized sensor is mounted and may be attached to the corewire near its distal tip in a flexible distal segment. The electrical conductors connect to this sensor and are routed within the internal channel or channels of the corewire to a proximal connector or interconnecting subassembly. The flexible distal segment of the device has a tapered corewire of a smaller diameter, by design to offer increased flexibility where desired, that may eliminate the need for the internal channel or channels to extend the full length of the corewire. The flexible distal segment may be formed from the same corewire material or from different corewire material that is joined to the proximal segment. The electrical conductors can be placed adjacent to the corewire of the flexible distal segment or loosely wound in a spiral pattern around the flexible distal segment of the corewire.

A spring coil or sleeve can be placed over the electrical conductors and corewire to contain the conductors within the boundaries of the device's overall diameter in the flexible distal segment where the corewire diameter is reduced. Components may be bound to the corewire with provisions to allow for free movement of the electrical conductors through the bond joints. Importantly, the overall diameter of the device is maintained at or less than the specified maximum needed to transport compatible devices like catheters or stents over the guidewire body. For coronary guidewires, this diameter is less than approximately 0.014 inches or 355 microns.

The diameter of the corewire is maximized by containing the conductors within the internal channel or channels of the corewire, and avoiding use of an additional covering surrounding the entire corewire diameter. This enables the maximum diameter corewire. While this design creates special challenges in manufacturing, manufacturing methods have been optimized to enable high volume, efficient manufacturing which offers the potential to greatly reduce the manufacturing costs normally associated with sensor guidewires.

DESCRIPTION OF DRAWINGS

FIG. 7A shows a cross sectional view, taken along the line B-B of FIG. 6B, of an outer strip of material being seated over the electrical conductor wires within a closable channel of the corewire prior to closing the channel during manufacturing.

FIG. 7B shows a cross sectional view, taken along the line C-C of FIG. 6B, of an assembled corewire formed from the outer strip of material and corewire with the electrical conductor wires contained within the closed internal channel.

FIG. 9A shows a cross sectional view, taken along the line D-D of FIG. 8, of an outer cover being seated over the electrical conductor wires within a closable channel of the corewire prior to closing the channel during manufacturing.

FIG. 9B shows a cross sectional view, taken along the line E-E of FIG. 8, of an assembled corewire formed from outer cover and corewire with the electrical conductor wires contained within the closed internal channel.

DETAILED DESCRIPTION

Figure 1:
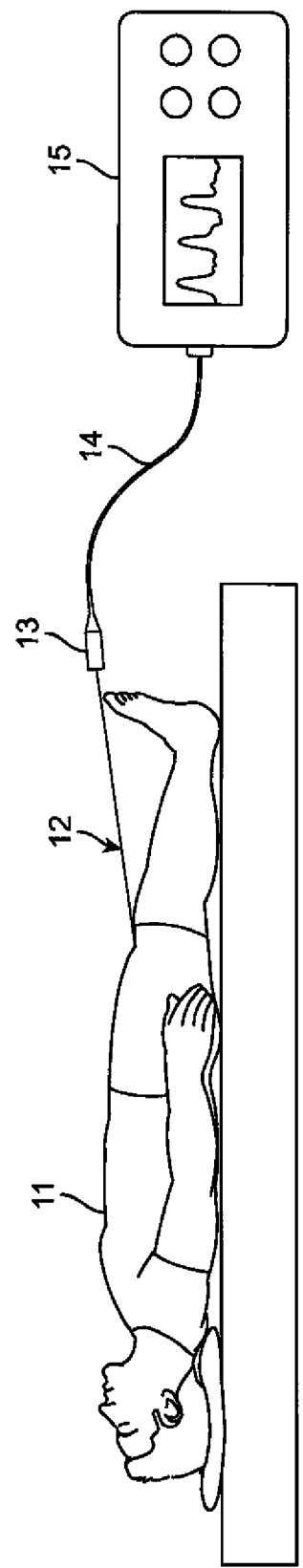
FIG. 1 shows a patient positioned supine on an operating table with the invention inserted into the body, a cable outside the body connecting the invention to an instrument and an instrument outside the body to display the physiological measurements.

The guidewire device 12 is a device capable of measuring physiological parameters within a body. As shown in FIG. 1, it is adapted for introduction into a body 11 through a puncture into a vessel and delivery through the vasculature. It is comprised of an interconnecting proximal subassembly 21, an intermediate corewire 22, and a distal flexible segment 23. The assembled corewire 24 is an elongate member with an internal channel or channels 41 housing electrical conductor wires 31 routed from the conductors 113 in the interconnecting proximal subassembly 21 to the sensor 28 mounted within the sensor subassembly 29. The electrical conductors or wires 31 provide communication of electrical signals from outside the body 11 to the sensor 28, and from the sensor 28 to an instrument 15 outside the body 11. An outer coating (not shown) to enhance lubricity or modify the surface friction of the device can be deposited on the outer surface of the sensing guidewire 12. The coating may be polytetrafluoroethylene (PTFE), also known by its trade name Teflon™, a hydrophilic polymer coating, parylene or other materials commonly used for coating guidewires. Spring coils 26 made from stainless steel or platinum can be mounted over the assembled corewire 24 in the flexible distal segment 23, where a reduced diameter solid corewire is preferred for flexibility in navigating tortuous coronary vasculature. A connector 13 to the sensor guidewire 12 is mounted on the proximal end of the device where it connects to the interconnecting subassembly 21. The connector 13 enables a physical engagement of the pressure sensing guidewire 12 to a cable assembly 14 and provides a means for transmission of electrical signals from the sensor 28, through the cable assembly 14, to an instrument 15 outside the body 11.

The corewire 24 can be constructed from diamond drawn, cold worked wire which offers enhanced tensile strength. The fabrication of cold drawn wire is known to those with ordinary skill in the art. A grade of stainless steel such as 302, 304V, 316 LVM or other grades are suitable materials. In one embodiment the stainless steel corewire serves as the base material for both the proximal corewire segment and the flexible distal segment, which is made flexible by a secondary grinding process to reduce the outer diameter. Alternatively, nitinol #1, nitinol #2 or nitinol #3 or other grades of nitinol could be used. Another alternative is to have a proximal corewire segment made of cold drawn stainless steel and a flexible distal segment made of nitinol. The cold drawn stainless steel proximal segment is joined to a tapered nitinol flexible distal segment. In this case, the proximal corewire segment is made of a different material from the distal flexible segment. It is anticipated that other combinations of materials, suitable for use as a guidewire corewire, can be used to construct the corewire assembly. Corewire materials suitable for this purpose are readily available from entities such as Fort Wayne Metals, http://fwmetals.com, or Lake Region Medical (Greatbatch), http://www.lakeregionmedical.com.

Figure 6A:
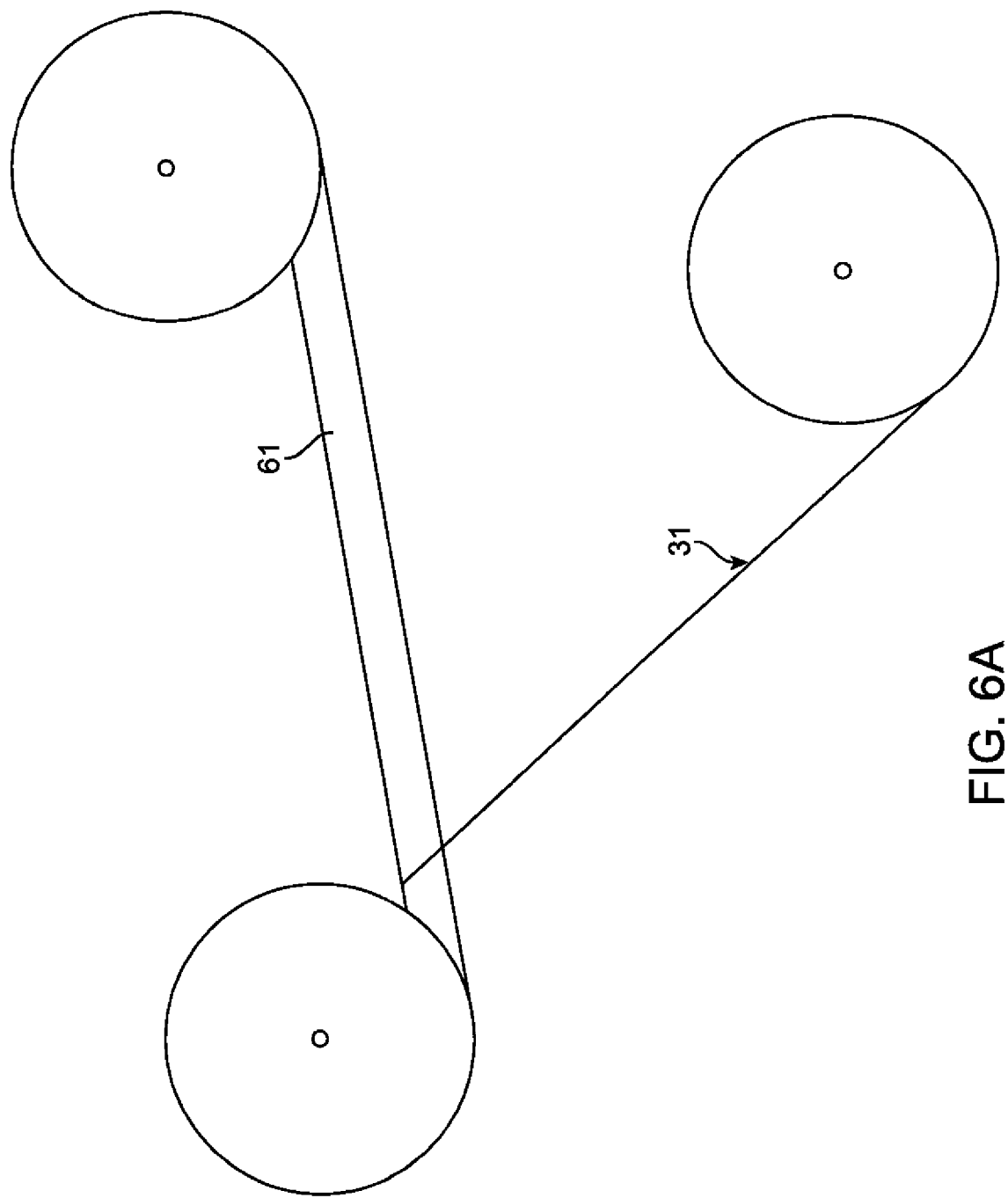
FIG. 6A shows a schematic depiction of a reel to reel continuous process for embedding electrical conductors within the channel of an open channel corewire, highlighting the device's suitability for efficient manufacturing processes.

An initial outer surface channel, or a closed internal channel 41, can be shaped during the cold drawing process to create the final internal channel or channels within the corewire 24. Where the closed internal channels 41 are formed during the manufacture of the drawn cold worked corewire, conducting wires 31 may be fed into the internal channels 41 post-processing. Alternatively, as shown in FIG. 6A, conducting wire 31 may be pre-placed within the open channel of the corewire 61 prior to formation of the closed internal channels. The closed channel can be formed after the wire drawing process as a secondary operation. This can be accomplished by grinding, laser etching, or any number of other comparable processes used to remove material. The final material properties can be tailored by a post forming process exposing the cold drawn wire to elevated temperatures and different gaseous atmospheres in an annealing process. Annealing is performed to optimize the properties of the corewire, including to reduce the brittleness of the hardened metal wire.

Figure 4:
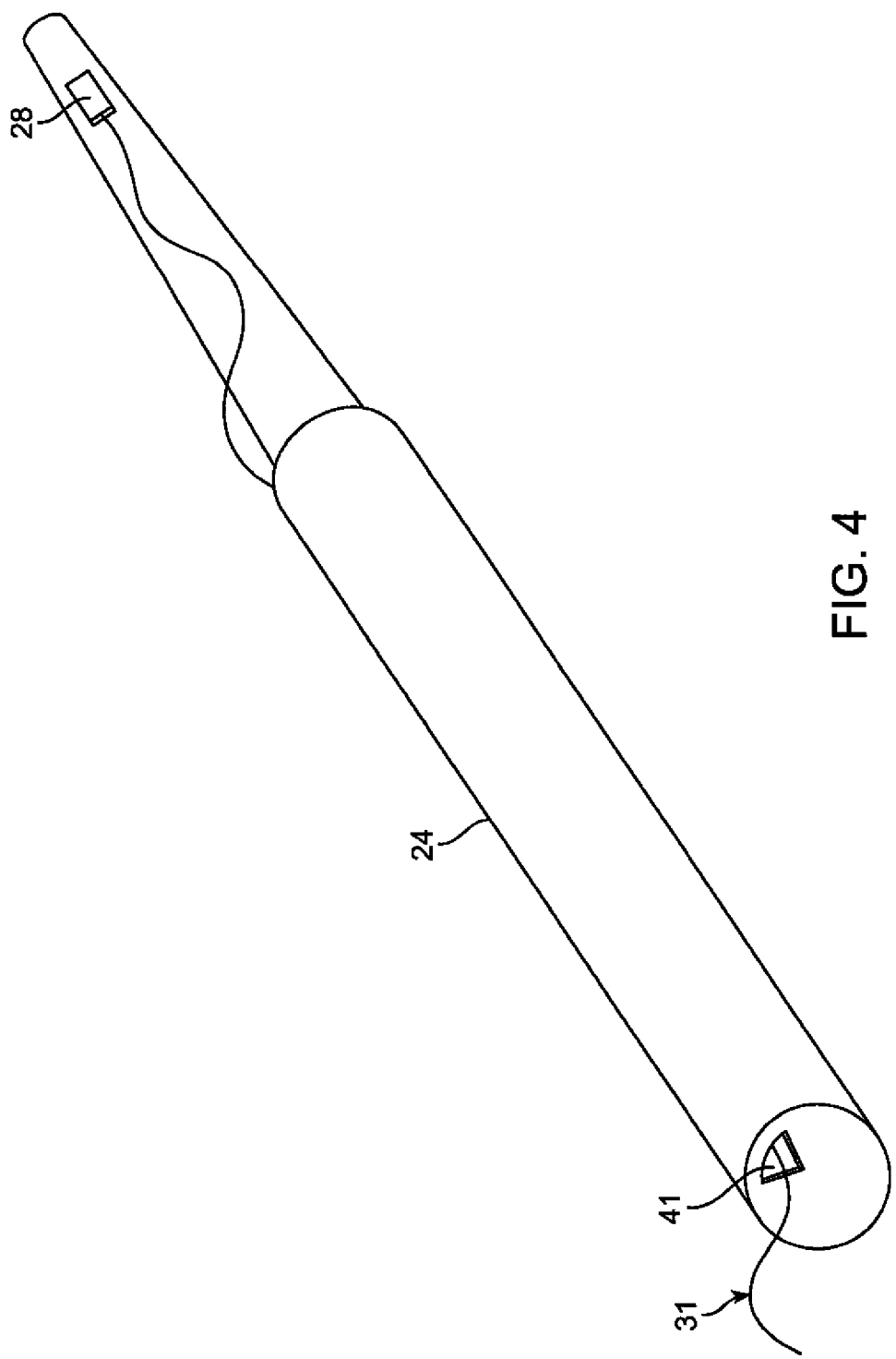
FIG. 4 shows an isometric view of the guidewire subassembly with the sensor wires shown extending from outside of the channel on the proximal end of the corewire and sensor disposed along the distal flexible segment.

Electrical conductor wires 31 are positioned within the internal channels 41, as shown in FIG. 4. Typically, 3-wire medical electrical cables or trifilar wires are used, which are commonly known to those of ordinary skill in the art from a variety of manufacturers. The internal channel may be sized in such a way as to permit free movement of the conductors within it. The maximum diameter of the corewire 24 is substantially the same as that of a standard solid corewire outer diameter. To accomplish such a maximum diameter, a cross-sectional profile is utilized such that the electrical conductors 31 are contained within the outermost surface diameter of the corewire. This provides for superior mechanical properties compared with prior art sensor wires. This minimizes loss in bend stiffness and torque of the final guidewire assembly. This structure enables superior lesion crossing and catheter/stent delivery capability in comparison with current FFR guidewires. The unitary structure also offers improved kink resistance, superior torque-ability and offers the operator similar tactile feedback to non-sensing guidewires.

To place the electrical conductors 31 within the channels 41 of the corewire 24, it is advantageous if the outer circumference of the corewire is formed around them. This can be accomplished by several processing techniques, including sealing a strip to cover the channel, as shown in FIGS. 7A-7B, where a strip 62 of cold drawn stainless steel can be inserted over or covering the channel and then processed to form a bond for sealing the strip within the corewire. The sequence of processing steps may include heat and pressure to seal the strip to the corewire. A secondary grinding operation can be used to reduce the outer diameter of the final assembly. Welding, soldering or other joining processes known in the art can be employed to create the bond. The strip 62 of stainless steel can take any number of shapes including circular, rectangle, an arc or a tube. In the event a tube, or stainless steel tubing sheath, is used in place of a solid metal strip, the tube may be pre-loaded to contain the electrical conducting wires 31. Such a pre-loaded tube may be used similarly to the thin metal strip 62, by placing it within the opening of the channel 71 and then processing it, through drawing and grinding or other processes known in the art, to rebuild the outer diameter so it is uninterrupted and contiguous. The end result is the formation of a closed internal channel 41.

Figure 8:
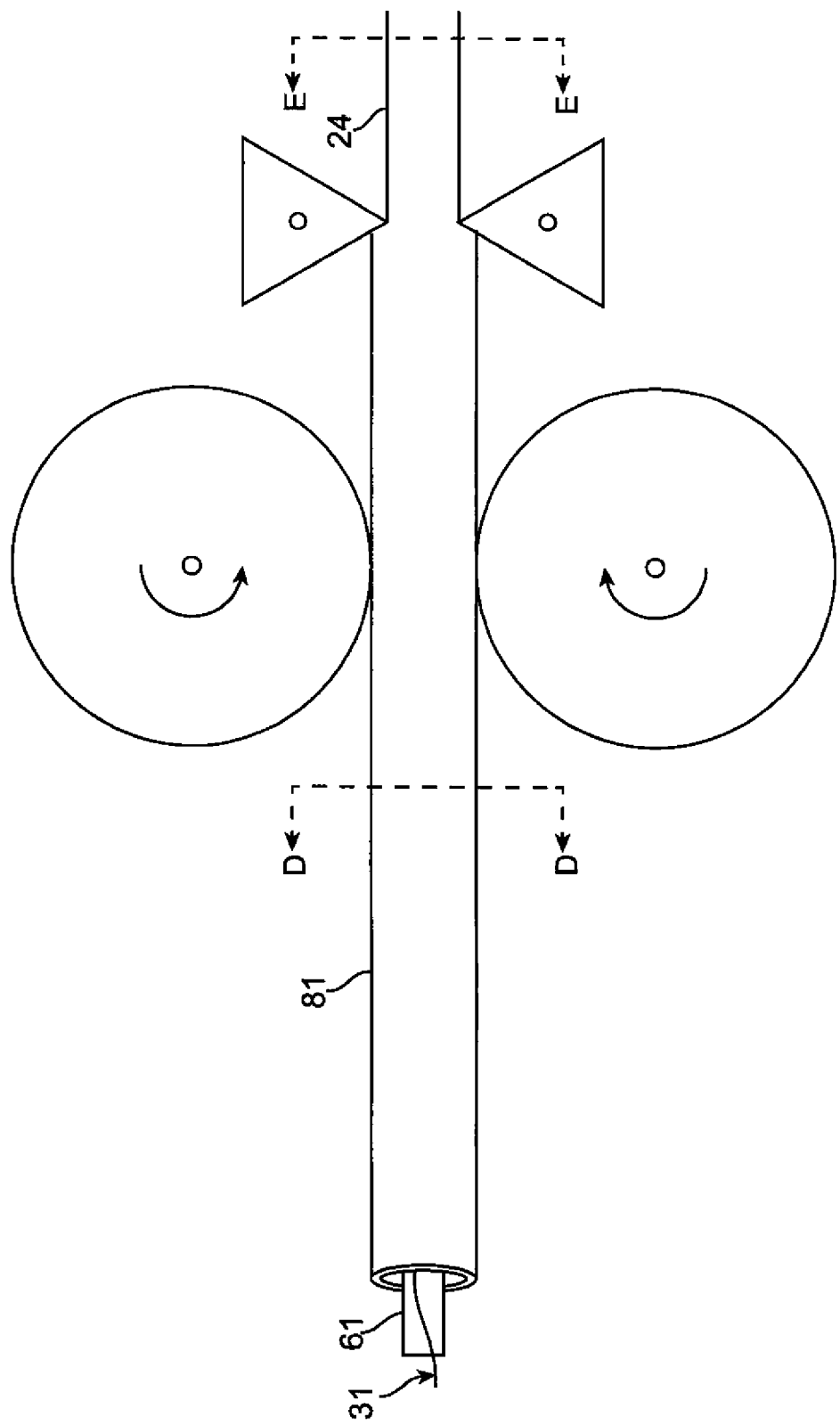
FIG. 8 shows a schematic depiction for an alternate process of forming the internal channel by drawing an outer cover, or tube, over the channeled corewire with conductors contained within the channel of the corewire.

Another method to accomplish this is to form a stainless steel tube around and on the solid corewire, as shown in FIG. 8, by drawing it through a die, or a series of progressive or reduction dies, to force a small amount of material into or covering the open channel. Thereafter, the outer diameter of the in-process subassembly may be reduced using common processes, such as centerless grinding. Importantly, this technique can be tailored to preserve the open space between the outer tube and inner solid corewire to allow free movement of the conductors. This seal may be created through interference fit, cold working, weld, or other joining methods familiar to those skilled in the art. Once the tube 81 is sufficiently joined to the corewire 61 and over the conductors 31, a secondary grinding process may be used to bring the oversized corewire down to the size of a standard corewire. At this point, the tubing once (or twice or more) compressed and applied around the circumference of the solid corewire has been completely removed from the corewire with the exception of a small amount of material inside the channel, along the lines shown in FIG. 9B, yielding the closed channel corewire 24. Alternatively, to obtain desired advantages during manufacturing such as a closer initial fit between the tube and corewire, a thicker or heavier walled tube may be used over the corewire, for example, approximately 0.003 inch tube wall thickness, as compared to a thinner tube wall thickness of approximately 0.0015 inches.

The preferred material for the strip 62 or tube 81 is the same as the solid corewire, which may be a desired grade of stainless steel or nitinol. This ensures nearly homogenous properties and promotes joining, regardless of the process used to join the materials. The final assembled corewire 24 is sufficiently circular and contains the electrical conductors 31 within its interstices or internal closed channels 41. The process can be performed in a continuous reel-to-reel process offering significant cost-savings. Prior art FFR devices are typically constructed in batch processes that are necessarily labor intensive and prone to manufacturing yield loss.

Alternatively, the centerless grinding process used with the present device, is intended to remove most of the outer tubing or strip, in order to improve flexibility, and can be controlled to leave a small amount of the tubing or strip intact, providing for increased sealing integrity. It is contemplated that other suitable materials can also be used for the strip, including metallic and polymeric materials, providing a protective seal and suitable for use in a continuous reel-to-reel process designed for low cost manufacturing. While using a continuous manufacturing process offers the potential cost savings, the design is also amenable to conventional batch assembly process techniques.

The sensor guidewire device design incorporating the aforementioned processed corewire 24 enables access across vascular blockages with a sensor 28 that can be attached to the flexible distal end of the corewire 23. The superior structural properties offered by use of a maximized corewire outer diameter obviates the need for the frequent guidewire exchanges often employed with current FFR devices thus reducing the cost and the time required to perform the procedure.

The closed internal channel 41 inside of the corewire provides a protected space for routing the electrical conductors 31 from the sensor 28 to equipment 15 outside the body 11. The internal channel 41 defined by the outer strip 62 and corewire 24 may be partially filled by the electrical conductors 31 to enable free and unencumbered movement so as to avoid tugging on the electrical connections to the sensor or other immobilized components as the device is advanced through the patient body. Alternatively, or additionally, extra electrical conductor wire 31 length in the flexible distal segment 23 of the device can provide freedom of longitudinal wire movement adjacent to fixed conductor wires within the internal channels 41. In this embodiment the extra length in the distal segment enables free movement where the guidewire is designed to be distorted by vascular anatomy, as the flexible distal end 23 is the first portion of the guidewire 12 that is advanced into a patient's body 11 through the most tortuous paths and blockages in the vasculature.

Figure 2:
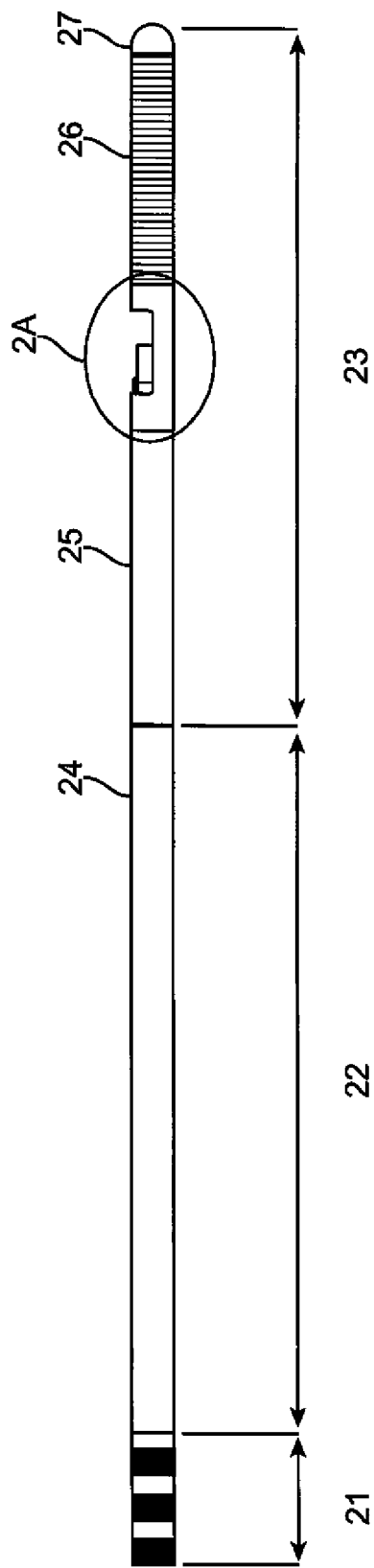
FIG. 2 shows the modular components of the guidewire device of the present application, including the interconnecting proximal subassembly segment, intermediate corewire (with internal channel), and flexible distal segment (with a sensor subassembly).
Figure 2A:
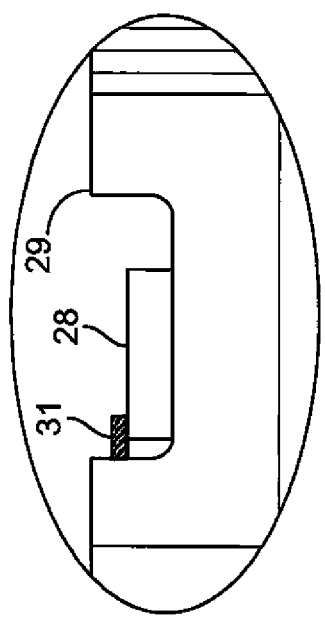
FIG. 2A shows an enlarged schematic view of the sensor subassembly highlighted in FIG. 2.

To secure the sensor to the guidewire, the current device affixes the sensor 28 to the guidewire 12 according to at least one of many techniques. Among these techniques is providing a sensor subassembly comprised of a cradle or tubular sensor subassembly 29 with an inner lumen of sufficient size to accept the sensor. The corewire 24 can be fixedly secured onto the sensor subassembly so that it can pass through to the distal most end of the device where it forms a distal tip 27, along with a surrounding spring sleeve or coil 26, as shown in FIG. 2.

Alternatively, to make room within the sensor subassembly 29, the corewire can be attached and terminated at the proximal section of the subassembly and a second wire affixed to the distal end of the housing. The surrounding sleeve 25 can be affixed to the corewire by a number of means including soldering or adhesive bonding. Likewise, the corewire can be attached to the sensor subassembly housing using similar bonding techniques. Other known bonding techniques have been contemplated. Electrical wiring 31 can likewise be connected to the sensor 28. By providing the sensor 28 and a completed sensor subassembly 29 electrical testing can be performed prior to final assembly, thus providing opportunity for cost savings. This sensor sub assembly structure can be easily attached to the aforementioned assembled corewire 24 subassembly enabling the sensor subassembly 29 to be used with different guidewire designs of the same diameter while benefiting from the savings of a guidewire utilizing high volume manufacturing. In other words, corewires of different designs can be easily interchanged with this modular sensor subassembly. This design reduces manufacturing cost and provides for a means to vary guidewire performance characteristics, enabling the manufacture of guidewires offering a variety of handling characteristics to better appeal to a broader group of users.

Current FFR guidewires have failed to provide the functionality of the current device due to an inability to successfully carry the signal from the sensor 28 to an outside instrument or monitor 15 without compromising the guidewire's vascular blockage crossing capability. The current device solves this problem.

FIG. 1 shows a patient 11 who is undergoing a procedure with the sensing guidewire device 12. The proximal end or segment 20 of the sensing guidewire 12 is attached to a connector or interconnecting subassembly 13 that provides the sensing guidewire with electrical interconnection and communication with an instrument cable 14. The flexible distal segment 23 of the sensing guidewire is inserted into the patient in this Figure, from whence it collects data that is transmitted via the instrument monitor cable 14 to an instrument 15. The instrument can also supply power to the sensing guidewire.

FIG. 2 shows the fully assembled guidewire device 12 in detail. It is separated into three discrete segments: interconnecting subassembly 21, intermediate corewire segment 22, and flexible distal segment 23. The device has completely internalized the electrical conductors 31 within the corewire 24. This enables both protection for the wires as well as optimization of the mechanical characteristics of the guidewire. A sleeve 25, sensor subassembly 29, and spring coil 26 are assembled over a section of corewire 24 with reduced diameter for increased flexibility, the flexible distal segment 23. The sensor 28 is shown within the sensor subassembly 29 guidewire. The interconnecting subassembly connects the sensor to an external monitor through wires 31 routed from the sensor to the connector 111.

Figure 3:
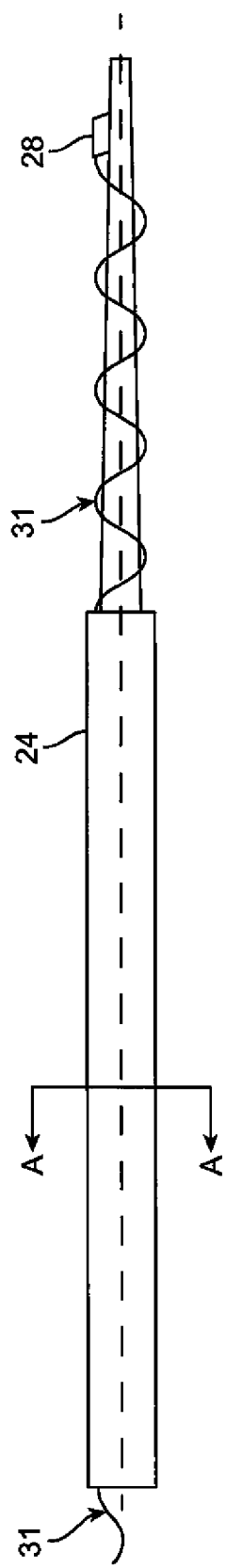
FIG. 3 shows a schematic side view of the guidewire subassembly with the electrical wires inside the corewire's internal channel and a sensor shown disposed along the flexible distal segment of the corewire.

FIG. 3 shows a subassembly of the sensing guidewire in more detail. The sensing guidewire includes an assembled core 24 that extends from the proximal end 21 towards the distal tip 27. The assembled corewire subassembly includes at least one internal channel 41 that extends from the proximal end 21 towards the distal end. In this figure, the channel is not shown as it is an internal feature of the corewire. The channel can be formed either asymmetrically, concentric, or parallel to the axis of the assembled core, or between those extremes. Other designs for the channel would be apparent to a person of ordinary skill in the art, including zigzag and wave shapes. Within the flexible distal end 23 of the sensing guidewire, the diameter of the corewire can vary, resulting in a tapered end. Towards the distal end of the tapered segment of corewire, a sensor 28 and, optionally, a sensor housing or subassembly 29 are secured. In one embodiment, the sensor is affixed in a cantilevered position with respect to the tapered section. Other embodiments would be readily apparent to a person of ordinary skill in the art, including affixing the sensor inside a separate tubular sensor housing at the distal end of the solid corewire or directly onto the distal end of the corewire, on a flattened surface. The tubular sensor housing can be made from materials similar to that used for the corewire, thus enabling the use of common bonding techniques like welding, soldering or bonding with adhesive.

At least one electrical conductor wire 31 runs from the sensor 28 near the distal tip to the proximal end of the corewire, spanning substantially the complete length of the device. In the preferred embodiment, three wires are contained in the channel 41, though configurations containing one, two, or more than three wires are also readily apparent to one of ordinary skill in the art. The preferred embodiment is a three wire configuration fused together to form a trifilar wire assembly. Medical wire of the type used are well known to those of ordinary skill in the art, and can be procured readily from suppliers like MWS Wire Industries, http://www.mwswire.com. Over the length of the sensing guidewire 12 that includes the closed internal channel, the conductor wire 31 lies within the channel. In one embodiment, the size of the channel is greater than the greatest diameter of the conductor wires 31 so that the wires can move freely, or slide longitudinally, within the channel 41. In another embodiment, the conducting wire is sized to fill the space within the channel 41.

FIG. 4 shows the assembled core at a different angle and closer perspective. In this embodiment, the assembled core includes a single triangular shaped internal channel 41, although in different embodiments the assembled core has other numbers of channels. The channel has a substantially triangular cross-sectional configuration, although other shapes would be obvious to a person of ordinary skill in the art, including U-shaped depressions of any height-to-width ratio (including zero) and rectangular openings. In one embodiment of the invention, the height of the channel is about 0.0028 inches and the width of the channel is approximately 0.0060 inches. In another embodiment, the ratio of the width of the channel to the height of the channel is about 2:1.

Figure 5B:
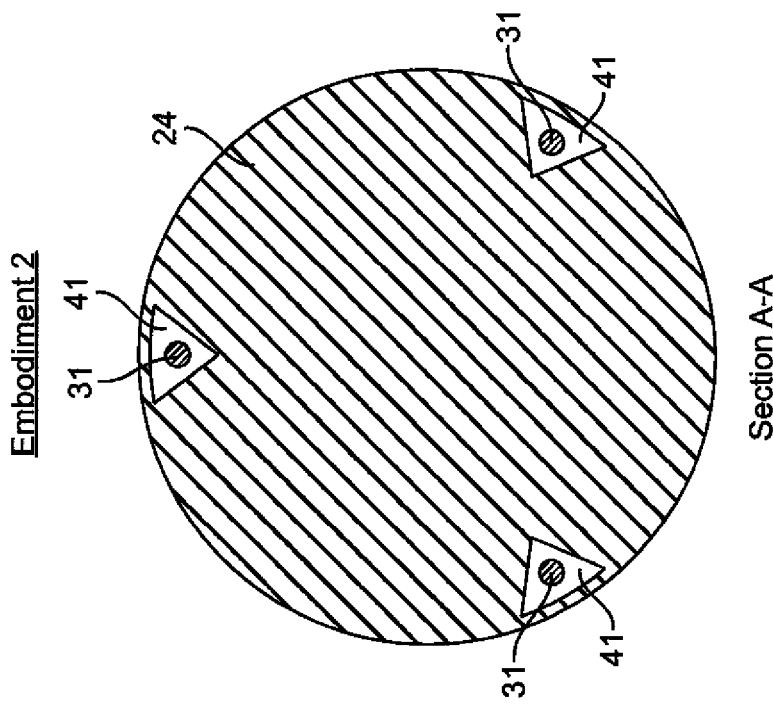
FIG. 5B shows a cross-sectional view of an alternative embodiment of the assembled corewire, electrical conductor wires placed within the internal channels, taken along the location of the line A-A of FIG. 3.
Figure 5A:
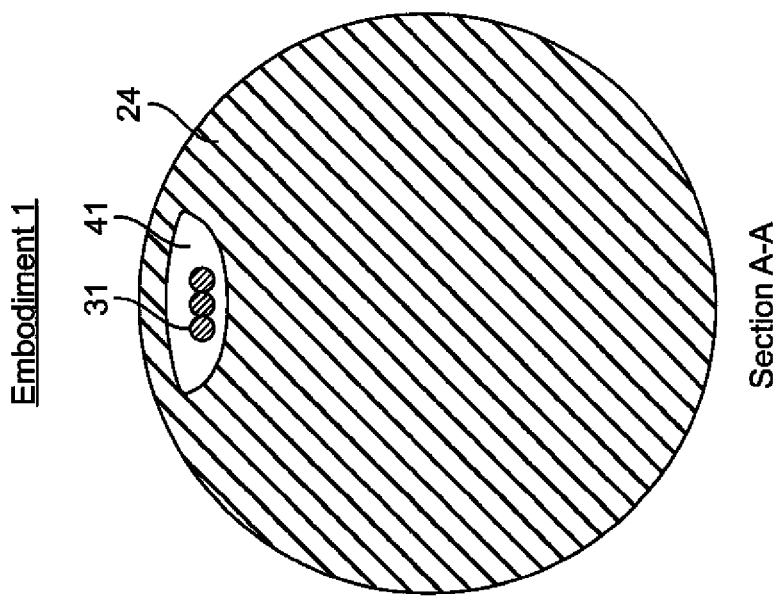
FIG. 5A shows a cross-sectional view of the assembled corewire, electrical conductor wires placed within the internal channels of the corewire, taken along the line A-A of FIG. 3.

FIGS. 5A and 5B show alternate cross-sections of corewire taken at the A-A plane in FIG. 3. The channel 41 is shown with sufficient space to enable the conductor wires 31 to move freely. In order to ensure the performance of the sensing guidewire, the at least one conductor wire is housed so it cannot easily break; since it is expected that the sensing guidewire will be bent, twisted, and otherwise deformed, the conductor wire or wires need to be protected from disconnection or breakage. In one embodiment, the conducting wire lies freely in the closed internal channel and has an overall length that, if straightened, is greater than the length of the sensing guidewire 12. When the sensing guidewire is bent, turned, or twisted, the conducting wire can move within the interstitial space defined by the channel 41. The channel can accommodate, over the length of the sensing guidewire, the additional length of the connecting wire. And when the sensing guidewire is bent in a direction that shortens the length needed for the conducting wires 31, the excess conducting wire can gather within the channel 41. Other techniques to protect conducting wires 31 from breakage include using coatings within the channel to reduce friction and/or covering the conductors with thicker layers of insulation. Adhering the conducting wires to other support materials, such as stainless steel, may also provide support during assembly and clinical use.

Figure 6B:
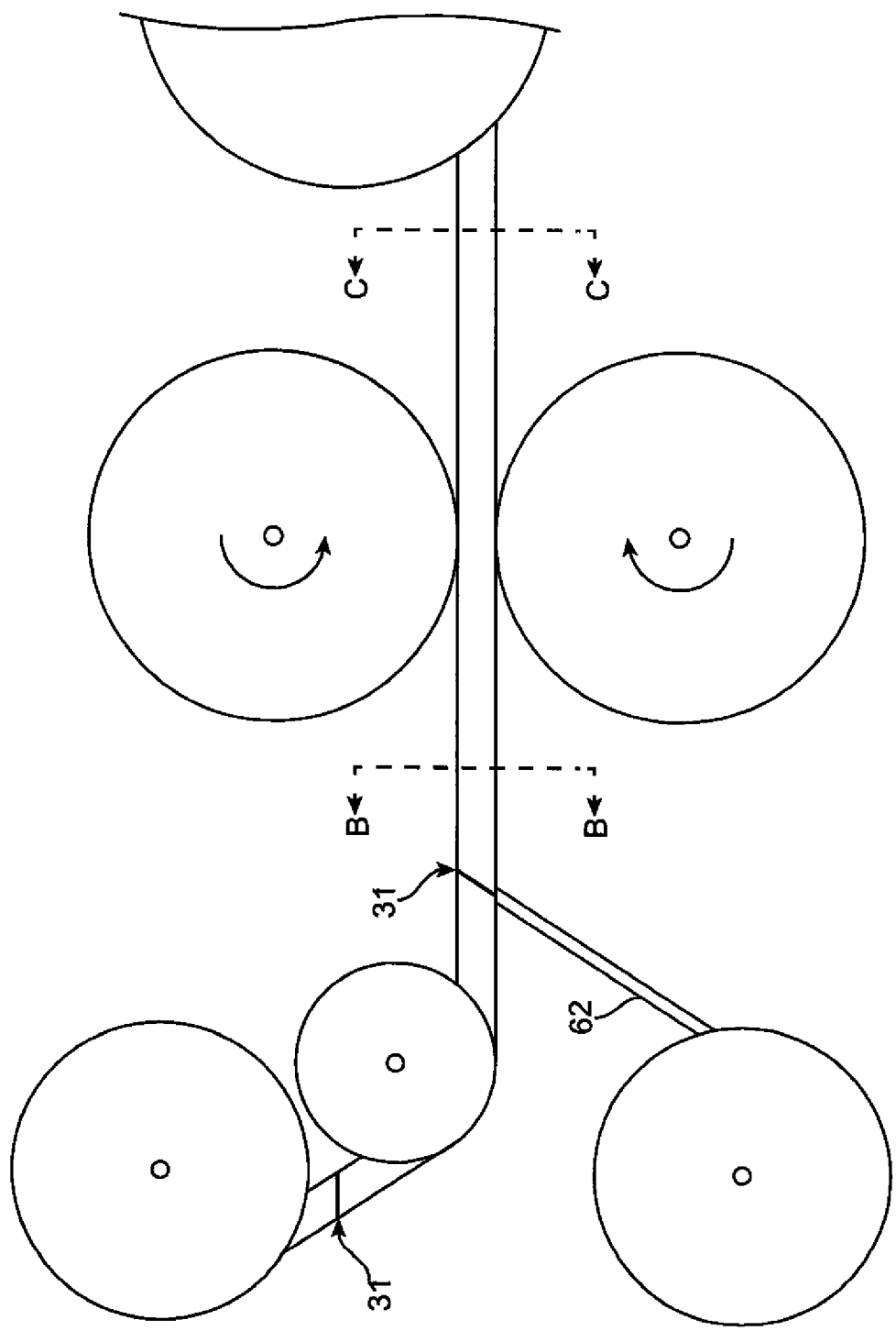
FIG. 6B shows a schematic depiction of a reel to reel continuous process for forming an outer strip of material over the open channel of an open channel corewire, forming the internal channel of the corewire within which the conductors are routed.

FIGS. 6A and 6B show steps of one possible continuous manufacturing process for assembling the electrical conductor wires 24 within the channel 41 of the corewire. In FIG. 6A a reel-to-reel process is shown where a channeled corewire 61 has electrical wires placed within the open channel such that they are within the outer diameter of the corewire. FIG. 6B shows an outer strip of metal material 62, in a preferred embodiment composed of a similar metal to that of the corewire, initially wrapped over top of the conductor wires 31 and seated on top of the open channel to form a closed internal channel 41. The strip is processed through grinding, cold working, or other processes familiar to those skilled in the art into a contiguous and homogenous outer surface of the solid corewire. It is anticipated that the strip can be formed from materials of varying shapes and dimensions, so long as they are able to be placed within the channel in a way that reliably forms the corewire internal channel 41 through the assembly process and provides for a robust seal and desired guidewire handling. In the preferred embodiment, a metal material such as stainless steel is used to close the internal channel, as it offers more protection and better space efficiency within the closed internal channel, as it is less fragile, and does not sag into the channel or abrade during use. However, various polymeric materials may be suitable for this purpose, for example polyimide or thermoplastic polymers such as PET (polyethylene terephthalate), nylon, polyurethane and co-polymers of these materials, such as polyether block amide (PEBA) such as PEBAST, commercially available from Arkema, or a polyester block co-polymer such as HytrelT, commercially available from DuPont. Likewise, polyether polyurethanes with carbon atoms linked in open chains, for example paraffins, olefins and acetylenes, such as TecoflexT, commercially available from Lubrizol, may also be suitable. Still further polymer materials from the polyurethane class of thermoplastic polymers such as PellthaneT, available from the Dow Chemical Company, and Tecothane, available from Lubrizol, may also provide alternative solutions.

FIGS. 7A and 7B show cross-sectional views of the process described in FIG. 6B. In FIG. 7A, the cross-sectional view at plane B-B in FIG. 6B, the strip 62 is shown seated on top of an open channel 71 containing the electrical wires 31. In FIG. 7B, the cross-sectional view at plane C-C in FIG. 5B, the same strip 62 has been joined to the corewire to form the assembled corewire 24 with an internal channel 41.

FIG. 8 shows another continuous process for assembling the electrical wires within the corewire's closed internal channels 41. In this process a metal tube 81 is placed over top of a corewire with an open channel 61, electrical conductors 31 contained within the channel. The tube is drawn down on top of the corewire through a die, effectively joining it to the outer surface of the corewire to form an assembled corewire with internalized channels 24. This corewire may then be ground down to a standard guidewire diameter. The majority of the tube 81 is effectively removed from the corewire during this process. This effectively maximizes the corewire diameter. In an alternative embodiment, a small amount of the tubular outer layer may be left in place to enhance the integrity of the sealed internal channel.

FIGS. 9A and 9B show cross-sectional views of the process described in FIG. 8. In FIG. 9A, the cross-sectional view at plane D-D in FIG. 8, the tube 81 is shown concentric to the corewire with an open channel 61, covering the channel containing the electrical wires. In FIG. 9B, the cross-sectional view at plane E-E in FIG. 8, the tube 81 has been joined to the corewire and then ground away to form the assembled corewire with an internal channel 41.

Figure 10:
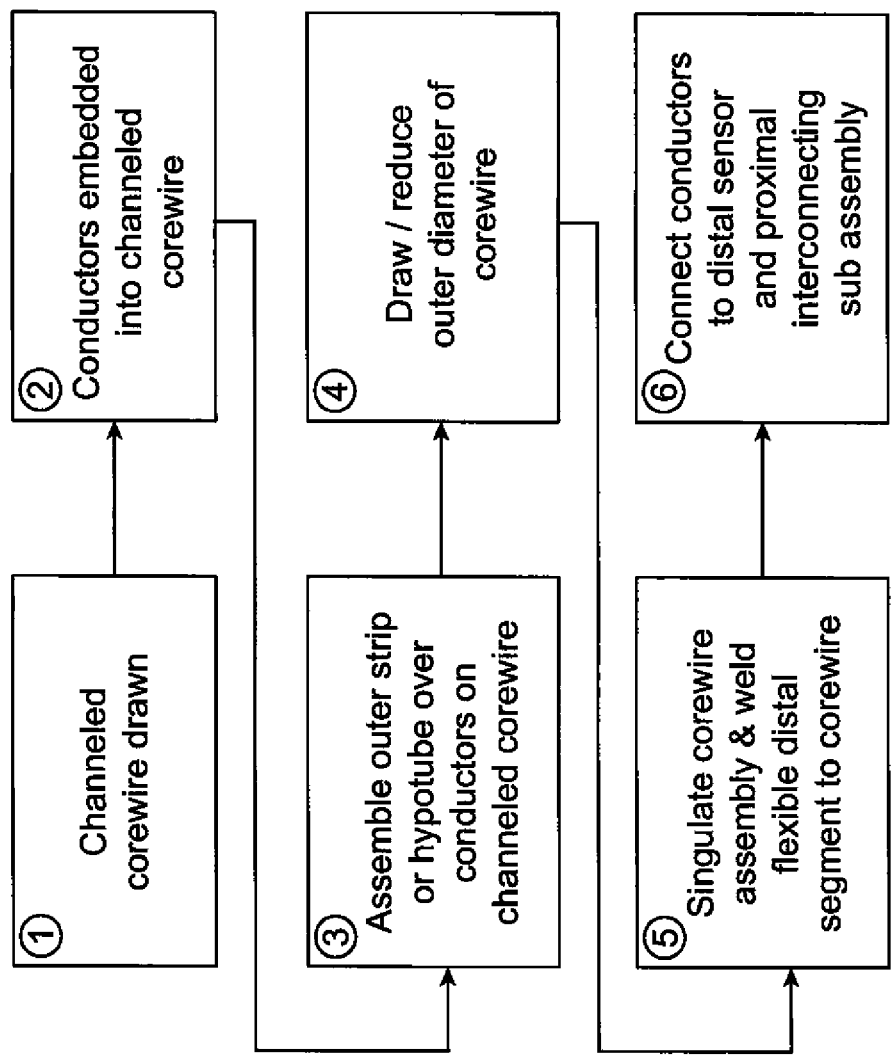
FIG. 10 shows a process flow chart for assembly of the guidewire.

FIG. 10 shows a process flow chart for assembling the guidewire using the corewire and electrical conductor wires. This process is one example that may be employed. Other processes may be employed to achieve the same end. For example, a method for manufacturing the sensing guidewire device is also contemplated where stainless steel wire is drawn through a die or dies, and the resulting cold drawn corewire forms a closed internal channel having a cross-sectional configuration which is off-set from a central axis of the corewire and has a sufficient size to enable free movement of a conducting wire positioned within the closed internal channel, and a conducting wire is fed through the closed internal channel of the corewire from a distal end to a proximal end. Optionally, the loose fitting conductor can be partially pulled out from the corewire to enhance processing. Processes may include soldering or bonding to other conductor segments.

Figure 11:
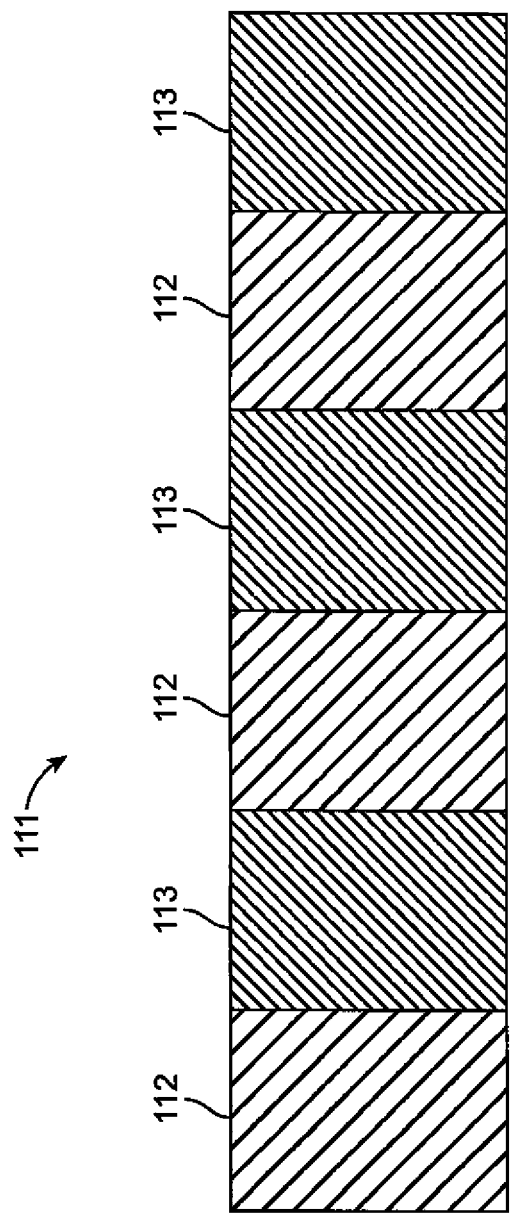
FIG. 11 shows an electrical connector composed of assembled alternating conductors and insulators assembled into one contiguous part.

FIG. 11 shows an embodiment of a solid plug style connector 111 with alternating bands of insulators 112 and conductors 113. These individual components of the solid plug are joined together with adhesive or other means.

Figure 12A:
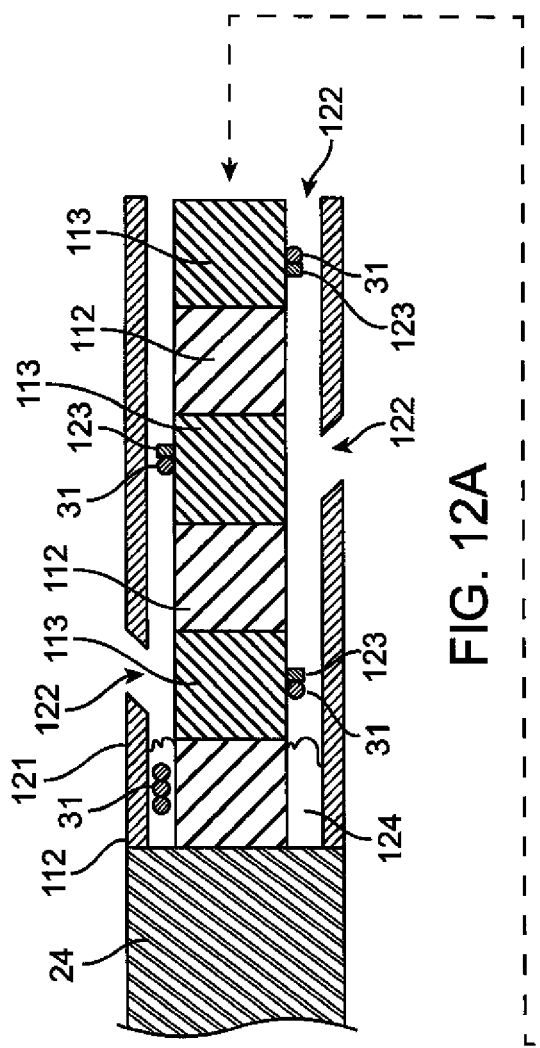
FIG. 12A shows an electrical connector integrated into the proximal end or segment of the guidewire.
Figure 12B:
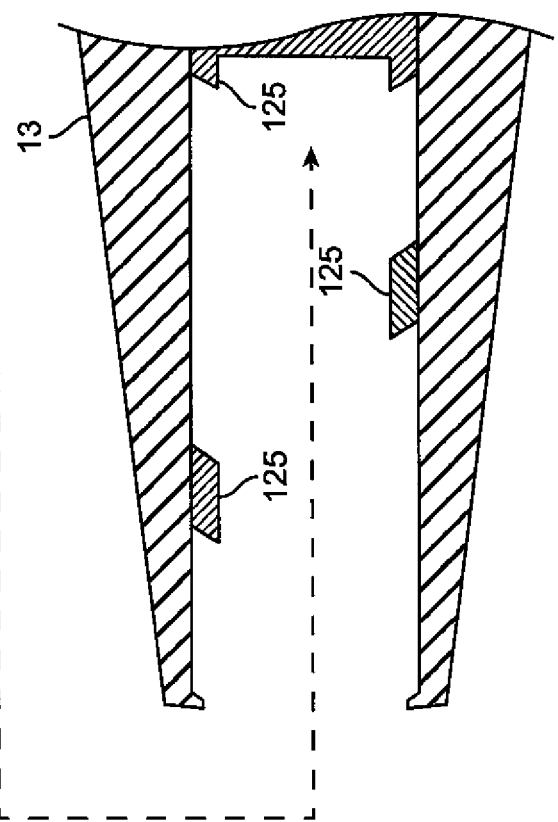
FIG. 12B shows a receiving connector with electrical contacts that completes the connection between the sensor and display system when the receiving connector is engaged with the electrical connector.

FIG. 12A shows an embodiment of a cylinder or solid plug 111 located within the internal diameter of an insulated solid plug covering 121. This solid plug 111 is constructed to function as a part of the corewire 24 by providing mechanical support for the interconnecting subassembly 21. The solid plug 111 may be joined to the corewire 24 and covering 121 with an adhesive 124 or through other conventional means. The interconnecting subassembly 23 is slid inside the connector 13, shown in FIG. 12B, to electrically connect the sensor 28 to an external instrument 15. In this embodiment, the solid plug includes alternating insulators 112 and conductors 113. The conductors 113 can be made from, for example, a platinum alloy (Pt—Ir); the insulators can be made from, for example, a polymer such as PEEK. While the insulators and conductors are shown here as having substantially identical diameters, the insulators could be made thinner than the conductors and vice versa. As shown in FIG. 12A, each conductor 113 is in electrical communication, through a solder joint 123 or other contact, with one of the electrical conducting wires 31 or one lead from a conducting wire that includes multiple leads. The wires 31 are shown to be wound around the outer diameter of the plug several times, but can be arranged without winding in other embodiments. For example, another embodiment of the solid plug 111 may have an irregularly shaped outer diameter in order to allow for the wires to lay within the maximum diameter of the solid plug. The electrical wires contained within the internal diameter of the body of the outer insulating cover 121 are visible once the solid plug is placed within this recessed area. This allows for simpler manufacturing of the connections between the wires and the conducting elements of the solid plug.

The solid plug conductors 113 are electrically connected to the wires 31, through solder joints 123 or other electrical interconnections, and engage with the connector 13 along connecting pins 125 when the connector 13 is engaged over the covering 121 along the line shown in FIG. 12A/12B. The connecting pins 125 are each designed to contact one of the solid plug conductors 113 through openings 122 in the solid plug covering 121. The pins 125 may be spring-loaded to facilitate engagement and removal of the connector 13. In place of pins flexible metal wires may be used. There must be at least three openings 122 in the solid plug covering 101 shown in FIG. 10A, including an opening on the most proximal end of the covering formed by the inner dimension of the tube, but other embodiments may include more to assist in creating an electrical connection so long as they do not overlap the path of the electrical wires 31. The openings 122 help locate and secure the connector 13 onto the guidewire and also help seal the connection between the solid plug conductors 113 and connecting pins 125 from disturbance by outside fluids or debris. In another embodiment of the sensing guidewire, the solid plug is part of the connector and is slid into the recessed area of the guidewire during a clinical procedure.

While other benefits of this solid plug connector concept will be apparent to people of ordinary skill in the art, some of the benefits are that a solid device provides a more robust connection between the sensing guidewire electrical wires and the connector. In addition, the area of electrical connection is protected within the recessed area, thereby preventing short-circuits caused by fluids such as blood. A further improvement provided by the solid plug connector is to facilitate manufacture by making it easier to visualize where the connecting wires connect with respect to the conductors.

Certain embodiments of the invention have been described with specificity in order to improve understanding of the invention. However, many variations and modifications will become apparent to a person of ordinary skill in the art. It is therefore expected and intended that the certain changes and modifications may be practiced which will still fall within the scope of the appended claims.

We claim:

1. A sensing guidewire device for measuring physiological parameters in a living body comprising:
    an elongate solid corewire member having a central axis, a length, an exterior surface, a proximal end, a distal end, and the elongate solid corewire member includes a channel which is offset from the central axis of the elongate solid corewire member, the channel extends through the elongate solid corewire member from substantially the proximal end to the distal end, the channel has an elongate opening formed within, the opening extending along and spaced from the central axis of the elongate solid corewire member, the opening is covered and closed by a metal strip bonded to the exterior surface of the elongate solid corewire member to form an internal closed interstice formed within the elongate solid corewire;
    a sensor disposed towards the distal end of the device; and
    at least one conducting wire that partially fills the internal closed interstice.

2. The sensing guidewire device of claim 1, wherein the at least one conducting wire partially filling the internal closed interstice freely moves and slides within the channel during bending movement of the sensing guidewire device during measurement of physiological parameters within a living body.

3. The sensing guidewire device of claim 1, wherein the sensor disposed towards the distal end of the device is an electrophysiological measuring sensor.

4. A sensing guidewire device for measuring physiological parameters in a living body comprising:
    an elongate solid corewire member having a central axis, a length, an exterior surface, a proximal end, a distal end, and the elongate solid corewire member includes a channel which is offset from the central axis of the elongate solid corewire member, the channel extends through the elongate solid corewire member from substantially the proximal end to the distal end, the channel has an elongate opening formed within, the opening extending along and spaced from the central axis of the elongate solid corewire member, the opening is covered and wherein the channel is closed by a metal tube covering the exterior surface of the elongate solid corewire member to form an internal closed interstice formed within the elongate solid corewire;
    a sensor disposed towards the distal end of the device; and
    at least one conducting wire that partially fills the internal closed interstice.

5. The sensing guidewire device of claim 4, wherein the at least one conducting wire partially filling the internal closed interstice freely moves and slides within the channel during bending movement of the sensing guidewire device during measurement of physiological parameters within a living body.

6. The sensing guidewire device of claim 5, wherein at least three conducting wires partially fill the internal closed channel.

7. The sensing guidewire device of claim 6, wherein the conducting wires partially filling the internal closed channel are adapted to move and slide within the channel during bending movement of the sensing guidewire device during measurement of physiological parameters within a living body.

8. The sensing guidewire device of claim 4, wherein the sensor disposed towards the distal end of the device is an electrophysiological measuring sensor.

9. A modular sensing guidewire device for measuring physiological parameters in a living body comprising:
   a flexible distal segment having a sensor disposed towards and secured to a distal end of the device;
   an intermediate segment having an elongate solid corewire member with a central axis, a length, an exterior surface, a proximal end, a distal end adapted to engage the flexible distal segment, at least one internal closed channel which is offset from the central axis of the elongate solid corewire member, the channel extends through the elongate solid corewire member along the length from substantially the proximal end to the intermediate segment distal end, the elongate solid corewire member forms at least a portion of the channel, and at least one conducting wire that partially fills the internal closed channel, the internal closed channel is closed along the exterior surface from the proximal end towards the intermediate segment distal end by a metal material, extends from the proximal end beyond the length and is electrically connected with the flexible distal segment sensor; and
   an interconnecting subassembly comprising a connector engaged on one end with the proximal end of the intermediate segment, electrically connected to the at least one conducting wire extending from the proximal end of the intermediate segment, and engaged on an opposite end with an external instrument located outside a living body for measuring physiological parameters upon receiving sensed electrical signals from the flexible distal segment.

10. The modular sensing guidewire device of claim 9, wherein the internal closed channel of the intermediate segment is closed by a metal strip bonded to the exterior surface of the elongate solid corewire member.

11. The modular sensing guidewire device of claim 9, wherein the internal closed channel of the intermediate segment is closed by a metal tube covering the exterior surface of the elongate solid corewire member.

12. The modular sensing guidewire device of claim 9, wherein the at least one conducting wire partially filling the internal closed channel freely moves and slides within the channel during bending movement of the sensing guidewire device during measurement of physiological parameters within a living body.

13. The modular sensing guidewire device of claim 12, wherein the intermediate segment includes at least three conducting wires which partially fill the internal closed channel.

14. The modular sensing guidewire device of claim 13, wherein the conducting wires of the intermediate segment partially filling the internal closed channel are adapted to move and slide within the channel during bending movement of the modular sensing guidewire device during measurement of physiological parameters within a living body.

15. The modular sensing guidewire device of claim 9, wherein the sensor disposed towards and secured to the distal end of the device is an electrophysiological measuring sensor.

* * * * *